(12) United States Patent
Vincent (10) Patent No.: US 7,201,831 B2
(45) Date of Patent: Apr. 10, 2007

(54) IMPURITY DETECTION DEVICE

(75) Inventor: David Robert Vincent, Ferndown (GB)

(73) Assignee: Water Security and Technology, Inc., Fogelsville, PA (US)

( * ) Notice: Subject to any disclaimer, the term of this patent is extended or adjusted under 35 U.S.C. 154(b) by 578 days.

(21) Appl. No.: 10/355,271

(22) Filed: Jan. 31, 2003

(65) Prior Publication Data

US 2003/0173233 A1    Sep. 18, 2003

(30) Foreign Application Priority Data

Feb. 22, 2002 (GB) .............................. 0204186.1
Jun. 21, 2002 (GB) .............................. 0214367.5

(51) Int. Cl.
*G01N 27/404* (2006.01)

(52) U.S. Cl. .................. 204/416; 204/431; 204/229.4; 205/778.5; 205/780.5

(58) Field of Classification Search ................ 204/400, 204/409, 416, 431, 252, 229.4; 205/780.5, 205/778.5, 793
See application file for complete search history.

(56) References Cited

U.S. PATENT DOCUMENTS

| 4,661,234 | A |   | 4/1987  | Takahashi et al. |            |
|-----------|---|---|---------|------------------|------------|
| 5,016,201 | A | * | 5/1991  | Bryan et al.     | 700/267    |
| 5,474,660 | A | * | 12/1995 | Robins et al.    | 205/780.5  |
| 5,480,535 | A | * | 1/1996  | Kondo et al.     | 204/425    |
| 5,520,789 | A | * | 5/1996  | Takahashi et al. | 204/424    |

FOREIGN PATENT DOCUMENTS

| EP | 0359 158     | 9/1989  |
| EP | 0 637 381    | 9/1996  |
| EP | 1 260 813    | 11/2002 |
| GB | 2 290 617    | 1/1996  |
| JP | 5142177      | 6/1993  |
| JP | 6102234      | 4/1994  |
| JP | 10332629     | 12/1998 |
| WO | WO 96/25662  | 8/1996  |
| WO | WO 96/28728  | 9/1996  |
| WO | WO 98/22813  | 5/1998  |
| WO | WO 99/46587  | 9/1999  |

* cited by examiner

*Primary Examiner*—Kaj K. Olsen
(74) *Attorney, Agent, or Firm*—Douglas Gene Glantz

(57) ABSTRACT

There is provided a sample preparation device and method for preparing a sample of liquid for detection of impurities. First (40) and second (38) electrodes are provided, located for immersion in a liquid under test. A semipermeable membrane (42) is positioned to protect the first electrode (40) from a body of liquid under test (32). The semipermeable membrane allows the liquid under test to pass therethrough to reach the first electrode, while preventing solids carried in the liquid from reaching the first electrode, the first electrode being positioned to affect the liquid under test in the vicinity of a sensor (36). Particular embodiments feature a hydrophilic membrane to protect the electrodes from suspended solids in the sample, a thin electrode assembly to achieve a faster response and the addition of a heater for temperature control to achieve consistent detection conditions and improved anti-fouling properties.

19 Claims, 6 Drawing Sheets

IMPURITY DETECTION DEVICE

The present invention relates to methods and apparatus for detecting and measuring gases dissolved in liquids, particularly gases dissolved in liquids which return to their gaseous state under certain conditions of temperature and pH. More particularly, the present invention relates to methods and apparatus for preparing a sample of liquid for such detection and measuring.

The present application may be applied, for example, to the detection and measuring of the concentration of ammonium ions ($NH_4^+$) and ammonia molecules ($NH_3$) in water. The present invention may also be applied to the measurement of chlorine (Cl) or cyanide ions ($CN^-$) in water, or any example where a gas may dissolve in a fluid but be released in its gaseous state under certain conditions of temperature and pH.

PRIOR ART

Figure 1:
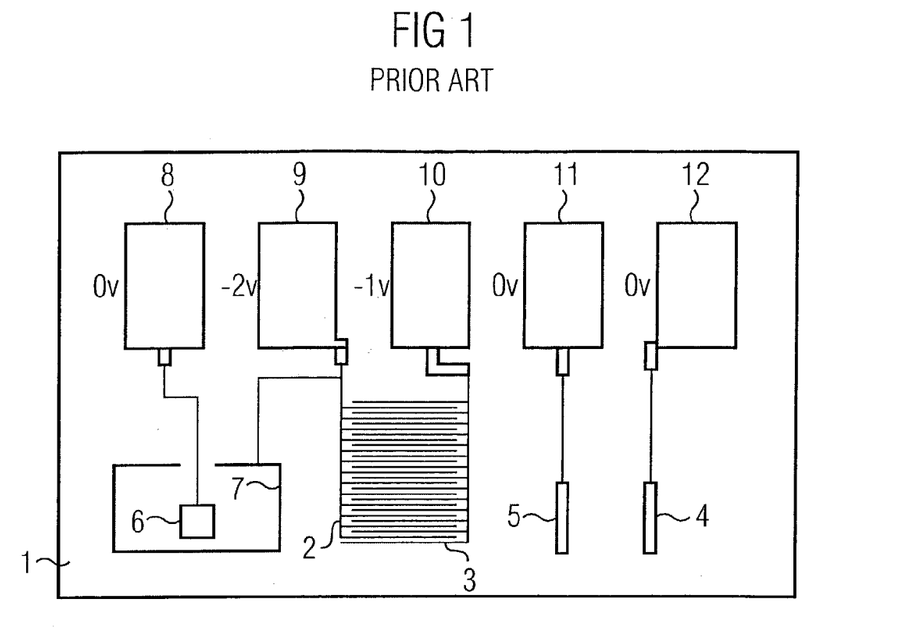
FIG. 1 shows a sensor device of the prior art for measuring dissolved species under controlled conditions of pH.

FIG. 1 schematically shows a water quality measuring apparatus as described in UK patent application GB-A-2290617. The illustrated device allows detection of dissolved species, such as chlorine or ozone in relatively clean water such as tap water. The sensor device comprises an insulating substrate 1 e.g. of ceramic, carrying interdigited electrodes 2, 3, a pair of counter-electrodes 4, 5, a reference electrode 6 and conductive pads 8–12 to connect the device to electrical measurement apparatus. The reference electrode 6 may be partly surrounded by a screen 7. The electrodes are typically of gold, or are gold plated. In use, a potential applied between electrodes 3 and 5 produces a current related to chlorine concentration, and a potential applied between electrode 2 and generator electrode 4 controls pH in the region of working electrode 3.

An example of a material that often needs to be measured is ammonia, which dissolves and dissociates in water according to the following reaction:

$$NH_3 + H_2O \leftrightarrows NH_4^+ + OH^-$$

At pH values below 8.0 the equilibrium is well over to the right. However, at higher values of pH (e.g. pH around 11), the equilibrium moves over to the left. In order to detect the ammonium ion concentration, it is possible to use a detector for $NH_4^+$ ions. However, such detectors can be unreliable, because they may also detect, for example, $K^+$ and $Na^+$ ions. Another possibility is to generate ammonia gas, by adding a suitable reagent containing hydroxyl ions (e.g. sodium hydroxide) to the liquid. The ammonia gas can then be detected using an ammonia gas detector.

Another material that it is often desirable to measure is chlorine, which dissolves and dissociates in water according to the following reactions:

$$Cl_2 + H_2O \leftrightarrows HOCl + HCl$$

$$HOCl \leftrightarrows H_+ + OCl^-$$

$$HCl \leftrightarrows H^+ + Cl^-.$$

In EP-B-0637381 there is disclosed an ammonia gas sensor which is housed within a container partially immersed in a solution containing ammonium ions. An electrochemical generator is provided to generate hydroxyl ions in a region of the solution adjacent the container. This converts ammonium ions to ammonia gas, which is sensed by the sensor after having diffused into a gas permeable membrane. This sensing provides an indication of the ammonium ions in the solution. This sensor is useful in a number of applications including testing for contamination in water. The addition of hydroxyl ions is achieved by means of the electrochemical generator, which generates hydroxyl groups according to the following reaction:

$$2H_2O + 2e^- \rightarrow 2OH^- + H_2 \uparrow$$

or $$2H_2O + O_2 + 4e^- \rightarrow 4OH^-.$$

WO-A-9625662 discloses a similar system. It also discloses apparatus for detecting chlorine levels, by generating hydrogen ions with an electrochemical generator, according to the following reaction:

$$2H_2O - 4e^- \leftrightarrows O_2 + 4H^+.$$

These documents disclose a method of detecting a material by increasing or decreasing the pH of the solution by electrochemical means. Thus, it is no longer necessary to add a reagent to the solution to increase or decrease the pH. However, there are problems with these methods. In particular, the liquid being analysed may be subjected to stirring, or, when there is a liquid flow, to flow variations caused by turbulence. This has the effect that the $OH^-$ ions generated at the cathode can be neutralised by $H^+$ ions generated at the anode.

Another problem is that in certain liquids the different concentrations of ions cause solids to precipitate upon the electrodes. A further problem is that, in certain liquids, stagnation encourages bacterial growth, or biological contamination, of the sensor by the accumulation of biofilms.

Figure 2:
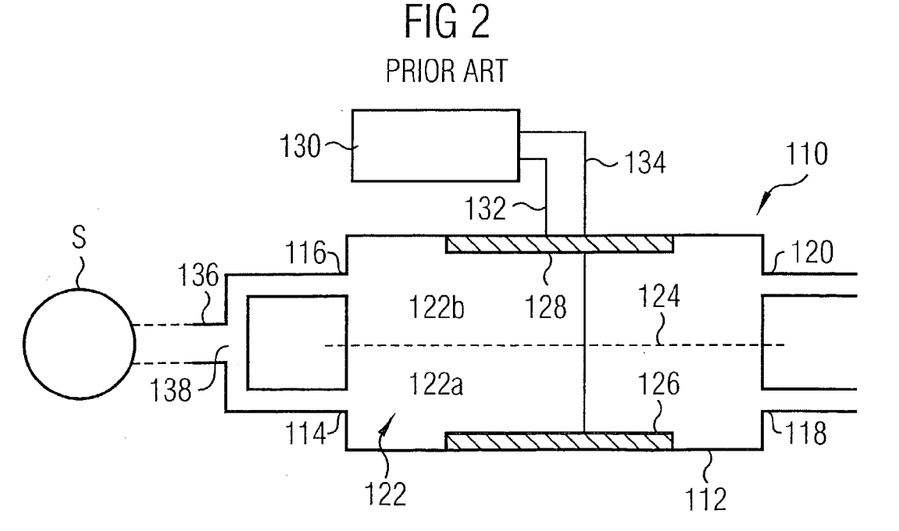
FIG. 2 shows apparatus for preparing separated solutions of controlled pH by electrolysis across a semipermeable membrane.

According to WO98/22813, there is provided a pH altering device as illustrated in FIG. 2. The device 110 comprises a receptacle 112 having liquid inlets 114 and 116 and liquid outlets 118 and 120. An interior 122 of the receptacle is divided into first and second chambers 122a and 122b by a microporous membrane 124 which extends across the interior 122. Each of the first and second chambers contains a respective electrode 126, 128. The microporous membrane 124 is arranged such that the chamber 122a is in fluid communication with the inlet 114 and the outlet 118, but is not in fluid communication with the inlet 116 and the outlet 120, and such that the chamber 122b is in fluid communication with the inlet 116 and the outlet 120, but is not in fluid communication with the inlet 114 and the outlet 118.

The electrodes 126 and 128 are electrically connected to an electrical power source 130 by wires 132 and 134.

The liquid to be analysed is flowed from pipe 136 to the flow splitter 138, where it is split into two separate streams, each of which is fed to a respective one of the inlets 114 and 116. The feed pipe 136 may be in communication with any suitable source of liquid, such as, for example, a river.

When a potential difference is applied across the electrodes 126 and 128 an electrical current flows through the liquid by virtue of the ability of anions and cations in the liquid to pass through the microporous membrane 124. The liquid stream fed to the chamber 122a comes into contact with the cathode 126. Upon the application of a potential difference from the source 130, hydroxyl ions are generated at the cathode 126. The generation of the hydroxyl ions increases the pH of the liquid in the chamber 122a and renders it relatively alkaline.

The liquid stream fed to the chamber 122b comes into contact with the anode 128. Upon the application of a potential difference from the source 130, hydrogen ions are generated at the anode 128. The generation of these hydrogen ions reduces the pH of the liquid in the chamber 122b and renders it relatively acidic.

The liquid stream in chamber 122a is discharged from the receptacle 112 via the outlet 118, and the liquid stream in the chamber 122b is discharged from the receptacle 112 via the outlet 120. The liquid stream discharged through the outlet 118 will be relatively alkaline compared with the liquid stream discharged through the outlet 120. If the liquid supplied to the device 110 from the pipe 136 were approximately neutral, then the pH of the liquid stream discharged via the outlet 118 would be greater than 7, and the pH of the liquid stream discharged via the outlet 120 would be less than 7.

A particular use of the device of FIG. 2 relates to fluid analysis. Broadly, this involves electrochemically modifying a region of the fluid to convert a material to be measured into a form in which its concentration can be measured (such as a gas), and sensing the amount of said form that is generated in order to provide a measure of the concentration of the material in the fluid. In this application the microporous membrane restricts or prevents any neutralisation caused by turbulence or mixing, so that an accurate measurement of the concentration can be obtained.

In order to use the device in chemical analysis, it is preferred to provide a sensing means in or downstream of the first and/or second chambers. In order to perform chemical analysis it is important for one or both electrodes to be capable of electrochemically modifying the fluid to convert a material of interest into a form in which it can be measured by the sensing means.

The sensing means may be adapted to sense ions in the solution (e.g. hypochlorite ions), or it may be adapted to sense a gas formed by the electrochemical modification (e.g. ammonia, carbon dioxide or sulphur dioxide gas).

When the sensor is a gas sensor it may include a membrane permeable to said gas, and detection means for detecting the amount of said gas that diffuses into the membrane. The gas-permeable membrane of the sensor may be any membrane that will permit the diffusion therethrough of the gaseous form of said material, but will prevent the passage of the fluid. The membrane may contain a dye sensitive to said gas, so that the concentration of the material can be measured by measuring the magnitude of the colour change of the dye. Means can be provided to measure the magnitude of the colour change.

The present invention is particularly applicable to the detection of species such as ammonia in very dirty water such as sewage or industrial effluent. The known devices suffer various problems in operating in such conditions. For example, the devices of FIGS. 1 and 2 would very quickly be fouled with solids to such an extent that the electrodes could no longer act on the liquid. The concentrations to be measured may be relatively low, and a flow-through device such as that of FIG. 2 would need to shift the pH of a large volume of water by a relatively large amount in order to release a sufficient quantity of ammonia to be measured. Furthermore, the solubility of ammonia varies considerably with temperature. Devices such as those of FIGS. 1, 2 would suffer from variation of temperature of the incoming fluid.

DESCRIPTION OF THE INVENTION

The present invention aims to alleviate at least one of the problems encountered with the devices referenced above. The present invention relates particularly to a device and method for preparing a sample of a liquid for detection of a dissolved species which reverts to its gaseous form under predetermined conditions of temperature and pH.

In particular, the present invention provides a device for detection of impurities in an impure liquid, comprising a first electrode and a second electrode located for immersion in a liquid under test; a semipermeable membrane positioned to delimit a sample volume from a body of the liquid under test, said semipermeable membrane allowing the liquid under test to pass therethrough to reach the sample volume, while preventing solids carried in the liquid from reaching the sample volume; and a sensor comprising a sensing element accessible to the sample volume. An integrated element, comprising a porous or permeable substrate carrying the first electrode and a heater, is provided within the sample volume.

The semipermeable membrane may also prevent the solids from reaching the second electrode.

The integrated element may further carry the second electrode.

The integrated element may itself comprise: a porous or permeable substrate; the first electrode formed on a first side of the substrate; and the second electrode formed on a second side of the substrate. The integrated element may further comprise a heater element located between one of the sides of the substrate and the corresponding electrode, the heater element being insulated from the corresponding electrode. The electrodes and the heater element may be formed by deposition of respective conductive layers onto the substrate.

The first and second electrodes may be planar and concentric, the first electrode being substantially circular, the second electrode being substantially annular, having an inside diameter larger than the diameter of the first electrode.

A gas volume may be provided between the first electrode and the sensor.

A gas permeable membrane may be provided to prevent the liquid in the sample volume from entering the gas volume, while allowing any gas emanating from the liquid to enter the gas volume.

A physical barrier may be provided between the first and second electrodes. The physical barrier may be porous or permeable to the liquid under test.

The device may further comprise a barrier around the first electrode, for restricting the movement of the liquid under test.

The device may further comprise a second heater for preventing condensation of vapour generated from the liquid under test.

The device may be arranged for use with an ion sensitive electrode as the sensor; alternatively arranged for use with a selective gas detector as the sensor.

The semipermeable membrane may be hydrophilic, at least on the side which is directed away from the sample volume. The gas permeable membrane may be hydrophobic.

The device may further comprise means for measuring and controlling at least one of the following characteristics of the liquid under test in the region of the first electrode: pH, temperature, conductivity.

The device may further comprise an outer housing to contain the electrodes, substrate, heater, membrane and sensor.

The present invention also provides a method of preparing a sample of liquid for detection of impurities, comprising the steps of: providing first and second electrodes within the liquid; applying a voltage between the first and second electrodes, to thereby create a region of increased pH and a region of reduced pH at the respective cathode and anode electrodes; and detecting a characteristic of the liquid in a first of the regions of hanged pH. The method further comprises the steps of: passing liquid from a body of liquid under test through a semipermeable membrane to reach the first region, thereby preventing solids carried in the body of liquid from reaching the first region, while allowing the impurity to be detected to reach the first region; and heating the liquid in the first region of changed pH to a constant temperature.

The temperature of the liquid in the first region may be adjusted to promote detection of the impurity to be detected.

The temperature of the liquid in the first region may be adjusted to deter the formation of biofouling on the membrane or on the electrodes.

The method may further comprise, in response to the alteration of the pH of the first region, converting the impurity to be detected into a gaseous form, and detecting the impurity with a suitable gas detector.

The present invention also provides, in isolation, an integrated element as defined above and having the first electrode formed on a first side of the substrate, with the second electrode formed on a second side of the substrate.

The above, and further, objects, advantages and characteristics of the present invention will become more apparent by consideration of the following description of certain embodiments thereof, in combination with the accompanying drawings, wherein:

Problems encountered with known devices include the fouling of the sensors and/or membranes, particularly when dealing with the detection of chemical species in waste water. Problems were also encountered in building up enough pH differential, or achieving or maintaining the required temperatures. Since the concentrations to be detected are low, there are problems in collecting a sufficient quantity of the species to be detected to enable reliable detection. This is particularly true of sensors in which the sample fluid may circulate, since the required pH will not easily be achieved, and the temperature will not stabilise.

The present invention therefore aims to relieve at least some of these problems, as will be discussed with reference to FIG. 3, which schematically represents a sample preparation device according to an aspect of the present invention.

According to the present invention, an impurity detection device 30 is provided, to collect a sample 46 of a fluid 32 to be measured, and to generate a gas sample 48 of the species under investigation. A suitable detector 36 is required, although this could be of any known form, and the construction and operation of the detector 36 itself does not form part of the present invention.

The present invention may be applied to detect any species which is soluble in a liquid, but which returns to a gaseous state under certain conditions of temperature and pH. A common example is ammonia, which often needs to be detected in waste water and at water treatment plants. In the following description, the detection of ammonia in water will be described, but this is in no way limiting of the scope of the invention.

A pair of electrodes 38, 40, current or voltage controlled, are used to locally (electrochemically) adjust the pH of the sample water. Near the electrode 40, the pH is changed beyond the value required to convert the measurand species to a more volatile form (in this example, to convert ammonium $NH_4^+$ to ammonia $NH_3\uparrow$), which evaporates and then is detected as a gas by detector 36, which may be a simpler method of detection for many species. The pH shifted region near the electrode 40 could become acidic or alkaline according to the species to be detected, and according to the polarity of the applied current or voltage. During operation, polarity of the electrodes could be reversed to perform a cleaning and/or auto-zeroing action.

For the detection of ammonia, the electrode 40 is used as the cathode, to raise the pH of the surrounding liquid, thereby rendering it more alkaline, to release ammonia gas:

$NH_4^+ + OH^- \rightarrow NH_3\uparrow + H_2O$.

A semi-permeable membrane 42 is provided to protect the electrodes 38, 40 from fouling by solids, and to reduce or eliminate bulk movement of the sample around the electrodes.

Whilst the membrane 42 allows the diffusion 44 of the measurand chemical, in this case $NH_4^+$, towards the sensing volume 46, it stops sample movement due to liquid currents from dispersing the pH-shifted volume near the electrodes. The membrane 42 could be hydrophilic or hydrophobic, and of varying porosity. In a preferred embodiment, the membrane is hydrophilic on the surface facing away from the sensor 36, and has a low adhesion for proteins. These characteristics will reduce bio-fouling, prolonging service intervals by reducing the need for cleaning or replacement of the membrane 42.

The required electrolytic pH shifting must take place in 'clean' water. The electrodes 38, 40 are housed behind semi-permeable membrane 42 to prevent the incursion of solids into the sensing volume 46 or onto the electrodes.

In operation, the measurand chemical 44, in this case $NH_4^+$, diffuses into the sample volume 45 near the upper, central electrode 40, which in this example is operated as the cathode. The excess of electrons at the cathode causes excess hydroxyl ions to be generated in the neighbouring region by the following reaction:

$2H_2O + 2e^- \rightarrow 2OH^- + H_2\uparrow$, or $2H_2O + O_2 + 4e^- \rightarrow 4OH^-$ Either of these reactions will cause an increase in $OH^-$ ions, leading to a reduced concentration of $H^+$ ions and an accordingly raised pH. Due to this raised pH and increased concentration of $OH^-$ ions in the liquid around the cathode 40, some of the dissolved ammonium ions $NH_4^+$ in the liquid around the cathode return to their gaseous ammonia form $NH_3$:

The generated ammonia gas evaporates 34 into a gas volume 48 underneath the gas sensor 36, where it can be detected. The volume of ammonia produced represents the concentration of ammonium ions in the original sample, since the volume of liquid under test will not change, being fixed by the sample volume 45.

A small gas volume 48 is preferably maintained in front of the gas sensor 36 to allow the measured gas to diffuse into contact with as much of the surface of the sensor as possible, and for the density (partial pressure) of the gas of interest to be as constant as possible over the surface of the sensor.

The gas volume 48 is preferably enclosed by a porous, gas-permeable ring 50, which allows the build-up of measurand gas, in this case ammonia, to a more concentrated level. By adjusting this porosity of the ring 50, the sensitivity and response time of the overall sensor equipment may be adjusted. In some cases the porous ring may not be needed, for example in high concentration applications, where sufficient gas is emitted for such collection to be unnecessary. A gas permeable membrane 60 is preferably provided, to delimit the gas volume 48 from the sample volume 45, and to prevent fouling of the gas sensor 36 by the liquid 32. This membrane may not be necessary, according to the type of detector 36 used.

A substrate 52 is provided to support the electrodes. It must provide a transverse passage at least for ions of the species to be measured, and preferably also for the liquid in which they are dissolved. This may be achieved by providing a substrate 52 which is porous or permeable, for example having an array of small holes in it, particularly in the central portion 54 to allow measurand species, in this case $NH_4^+$, to pass through. The substrate 52 should preferably be as thin as possible to improve sensor response time by minimising path length between the electrodes while keeping them separated. The substrate should also be chemically inert and resistant to extremes of acid or alkali, since a significant pH differential may exist between its two sides.

While the measurand species needs to be able to pass through the substrate, the passage should be as restricted as possible, to reduce the recombination between $H^+$ and $OH^-$ ions, which would otherwise cancel the generation of alkaline and acidic regions around the electrodes and accordingly prevent efficient detection of the measurand species such as ammonia.

The upper electrode 40 must be kept in closer electrical contact with the sample liquid 45 than with the lower electrode 38, in order that the ions generated around the upper electrode serve primarily to adjust the pH of the sample volume, rather than to pass an electric current between the two electrodes. The volume 45 around the upper electrode should be kept small, to allow a relatively large pH shift to be obtained. By making the volume around the other electrode 38 somewhat larger, the pH shift of the lower region will be lower, and the tendency for the generated $H^+$ and $OH^-$ ions to recombine will be reduced.

The electrode 40 and the volume 45 should each be quite thin, but of fairly large area. This allows a high ratio of electrode surface area to sample volume 45, in turn providing for a relatively large pH shift and effective ammonia release while maintaining a sufficient sample volume 45.

Selection of the type and form of electrodes may have a significant influence of the effectiveness of the detector as described. It has been found that electrochemical activity preferentially takes place at the parts of the electrodes closest to each other. By providing electrodes in the form of two parallel planar meshes, the surface area of the electrodes are increased due to the mesh form, and the maximum possible use is made of the electrodes by placing them with as much surface area as possible in a "nearest" position. This also ensures minimum resistance to current flowing between the electrodes.

The electrodes must be robust enough to withstand bubble formation, and must be resistant to chemical attack. They may, for example, be made from a noble metal, or carbon. In certain embodiments, they may be printed onto a porous, or perforated, alumina substrate.

There is a wide variety of electrodes that are suitable for use with the present invention. The electrodes may be simple planar units of conductive material. They may comprise a metal, carbon, a semiconductor (such as a metal oxide), a conducting polymer, or a composite of two or more of these materials. We have found that electrodes comprising vitreous carbon, platinum, gold or stainless steel are suitable; however, other metals, such as silver may be used instead. Composites of two metals, such as platinum coated on titanium may be used. The electrodes may comprise solid, woven, porous or thick- or thin-film printed electrodes.

Electrodes comprising a piece of metal gauze have been found effective.

Gaps, or porosity of the material 50, must be provided sufficient to allow the generated ammonia gas to escape from gas volume 48 after detection, and to allow fresh liquid 32 or measurand species to enter the sample volume 45. By controlling the size of such gaps, or the porosity of material 50, the sensitivity of the device may be adjusted. The inside of the housing 62 and material 50 must be chemically robust enough to resist the formation of sulphuric and hydrochloric acid (among others). This is a typical natural consequence of the elimination of ammonia from polluted water.

A heater, schematically represented at 56, is included on the substrate to control the temperature of the liquid within the sensing volume. Ammonia, along with certain other species of interest, becomes less soluble at certain temperatures, as well as certain ranges of pH. The vapour pressure of ammonia is quite low below 10° C., which temperature is common in natural and waste water supplies. By controlling both the pH and the temperature of the solution to achieve conditions of reduced solubility, a maximum proportion of the available ammonium ions will be converted to ammonia gas, enabling greater accuracy of measurement. By heating the liquid within the sensing volume to a controlled temperature significantly above the ambient liquid temperature, such as 45–60° C., the operating temperature will not be affected by fluctuations in the ambient temperature of the liquid under test. Heater 56 will heat the liquid in the measurement volume, and also the sample preparation unit of the present invention. This increased temperature should also reduce or eliminate bio-fouling on. the membranes 42, 60, particularly if the operating temperature is selected with this in mind. A temperature sensor, not shown in the drawing, and associated control circuitry, is preferably also provided, to allow accurate control of the temperature of the solution, particularly in the sample volume 45 around and above electrode 40. The heater 56 may be provided only in the sample volume 45, if desired, but a more extensive heater will be able to heat a larger proportion of the solution above membrane 42, which should lead to a more stable temperature, and may help to prevent condensation of vapour from the sample 45 as it leaves the device.

Heating of the liquid contributes to keeping the membrane(s) 42, 60 clear of bio-fouling. The high temperature and the acidic/alkaline environment is not suitable for biological growth.

By maintaining a constant temperature of the measured liquid, all measurements are known to be comparable, being taken under identical conditions of temperature. The temperature-dependent solubility of ammonia, for example, is rendered constant by measurement at constant temperature.

In some applications it may be necessary to place one of the electrodes outside the membrane, directly in the liquid 32. This could increase the pH shift inside the sample volume 45, partly by impeding the recombination of the $H^+$ and $OH^-$ ions by increased physical separation.

Figure 3:
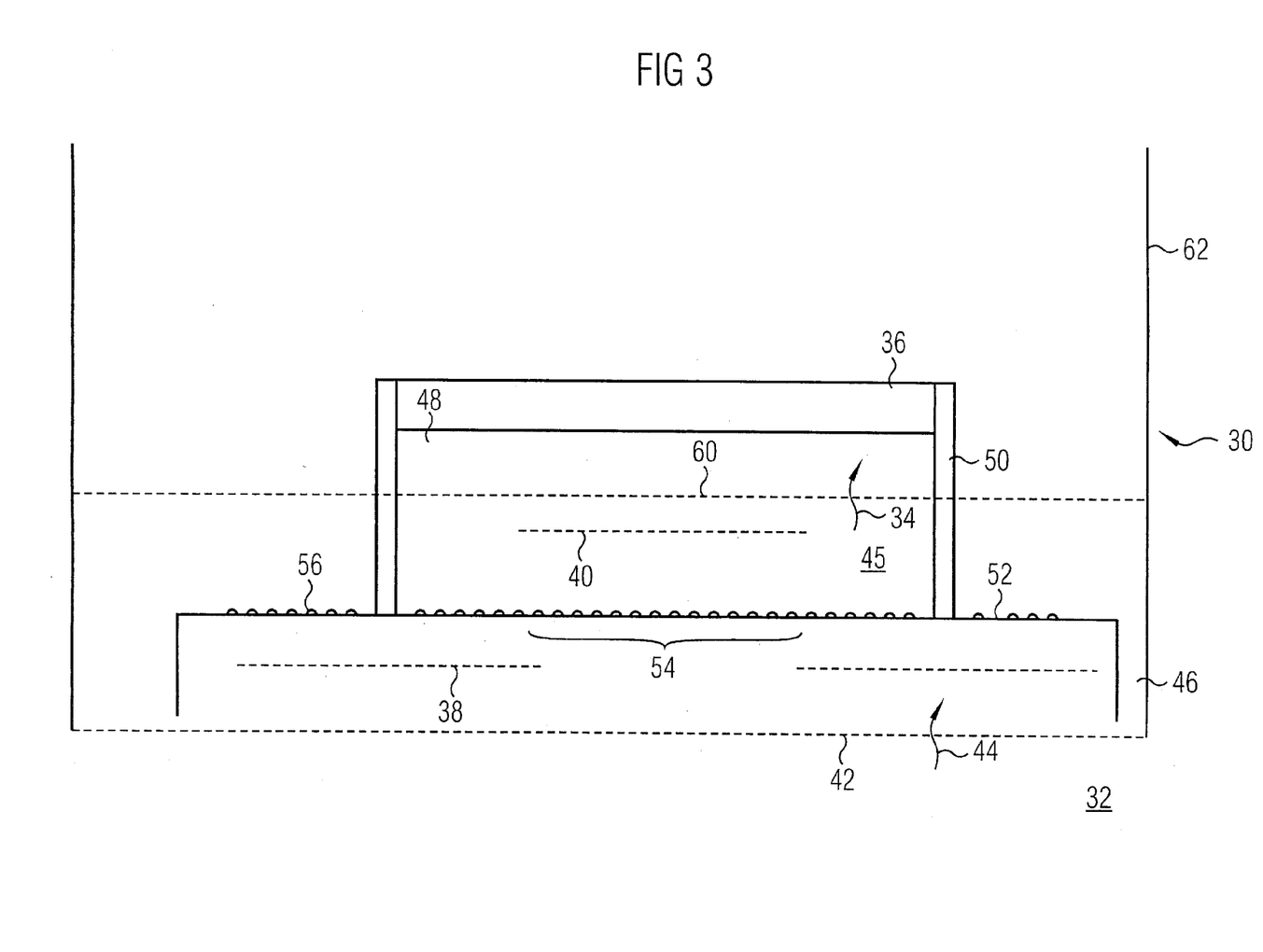
FIG. 3 shows a schematic representation of a sample preparation device of the present invention.

In the example illustrated in FIG. 3, the anode 38 could be placed outside the membrane 42, although it would then be subject to an increased likelihood of bio-fouling or accumulation of solids. The cathode 40 would remain within the membrane 42, where it can generate the required ammonia gas in proximity to the gas sensor 36.

The entire assembly of electrodes 38, 40, substrate 52, heater 56, membranes 42, 60 and sensor 36 may be enclosed within an outer housing 62. This housing could be formed of a solid sheet, which would prevent diffusion of liquid or the species under examination into the measurement volume 45 through such outer housing. Alternatively, a semi-permeable/porous membrane may be used instead, which would allow some in-diffusion of the liquid or ions under test through the outer housing 62.

Certain parts of the structure, for example the outer housing 62, the membrane 42 and the substrate 52, may need to be strengthened if used in a high pressure environment, or where a high pressure differential exists between the various parts of the test equipment. Such conditions may exist, for example, where the sensor is to be used in a water supply line, or within an effluent pipe.

The overall diameter of the unit will be limited by the ability to shift the pH of the sample and by the size of the gas sensor. The ability to shift pH will, in turn, depend on the nature of the electrodes, the potential difference applied between the electrodes, and the volume of liquid in the sensing region.

In an alternative embodiment, the gas sensor 36 may be replaced by an ion selective electrode (ISE) placed in one of the pH shifted regions, in order to detect the measurand species. Some species of interest may be more amenable to liquid phase sensing, and such an ISE could provide more sensitive or more accurate detection. Ion sensitive electrode sensing requires the provision of a reference electrode and an ion sensitive electrode, which will produce an output representative of the concentration of the ion detected, such as $NH_4^+$ or $H^+$.

Other sensors can be used instead. For example, other optical or electrical sensors may be used, and they may be invasive or non-invasive.

While the above-described embodiment creates an alkaline environment around the working electrode 40, other species of interest may require an acidic environment in order to return to their gaseous state. In such cases, the polarity of the potential difference applied between the electrodes is reversed. Electrode 40 becomes the anode, and creates hydrogen ions $H_+$ by the following reaction:

$$2H_2O - 4e^- \rightarrow O_2\uparrow + 4H^+.$$

This provides a region of increased density of $H^+$ ions, that is, an acidic zone, in the measurement volume. When the appropriate pH and temperature conditions are reached, the species of interest returns to its gaseous phase, and may be detected by a suitable detector 36. Alternatively, a liquid phase sensor such as an ion sensitive electrode (ISE) may be used to detect the species of interest while still in the dissolved state. When used in this way to detect a basic species, the sample surrounding the electrode 40 and next to the sample 45 will become acidic. This should help to keep the electrode 40 and membrane 60 clean.

It may be necessary to measure the pH in the sample volume 45 to achieve optimum control of pH. In certain embodiments of the present invention, the conductivity or other properties of the sample in the sample volume 45 could be measured to control the potential difference applied between the electrodes to achieve better pH control in the measurement volume.

In certain embodiments of the present invention, the electrode shapes could be varied to optimise pH differentiation, between the basic region around the cathode and the acidic region around the anode.

The electrodes may comprise metal film on ceramic; alternatively, they may be composed of gauze structures with solid or gauze insulating substrate layer in between.

The housing 62 needs to be constructed of a suitable material which should be resistant to fouling and also resistant to acidic and alkaline environments generated inside the unit. It should also be robust enough for installation in activated sludge aeration ponds.

Some active monitoring and control might be required, since no single current/voltage will be ideal for all liquids or species of interest.

FIGS. 4A–4F illustrate steps in the manufacture of an integrated element according to an aspect of the present invention. The integrated element includes the substrate 52, the heater 56, if any, the electrodes 38 and 40 and the necessary protective coatings and electrical connections to allow the integrated element to operate as a part of the detection apparatus according to the present invention.

Figure 4A:
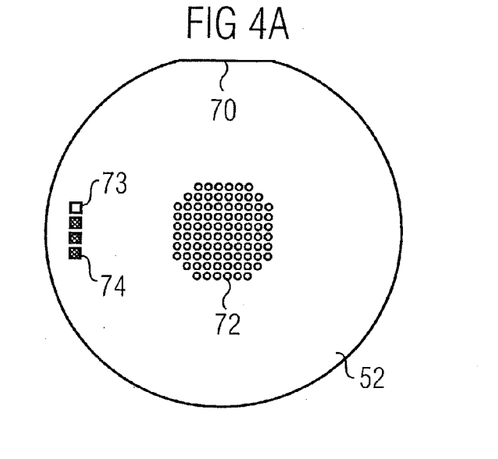
FIGS. 4A–4E illustrate progressive stages in the manufacture of an integrated element according to an embodiment of the present invention.

FIG. 4A shows a substrate 52 formed in a first step in the manufacture of the integrated element. The substrate comprises a circular disc of 96% alumina ceramic, of 635 μm thickness and 66.2 mm diameter. One or more flats 70 may be provided around the circumference of the substrate, to assist in orientation of the substrate during subsequent processing. An array of through holes are formed in a central region of the substrate. These holes may be 1 mm in diameter arranged on a square matrix at 2 mm pitch. Provision may also be made at this stage for later electrical connections to the various electrical components of the integrated element. For example, surface mount connection point 73 may be provided for electrical connection to features on the upper surface of the substrate, together with a through-plated holes 74 to provide electrical connection to the lower surface. The through hole and connection points may be at 2 mm pitch, offset from the edge of the substrate by 7 mm, and be gold plated. The integrated element may, of course, be produced to other dimensions, according to the materials used and the type of testing to be carried out.

Figure 4B:
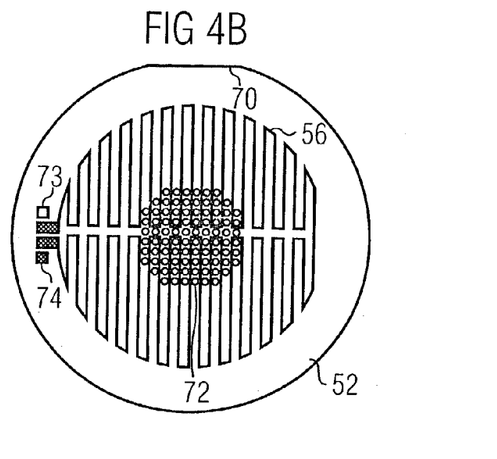

As shown in FIG. 4B, heater element 56 may next be provided on the lower surface of the substrate, for example by screen printing a resistive paste. The heating element may, for example, have a resistance of about 25Ω, and be of uniform profile. The terminals of the heater are provided in electrical contact with two of the through holes 74. As illustrated, the heater element preferably comprises a dual serpentine structure, arranged partially between the holes 72 and covering the majority of the lower surface of the substrate, in a circular region of about 54 mm diameter, concentric with the substrate itself.

The use of platinum electrodes printed onto opposite sides of a ceramic substrate has been found to be effective, robust and relatively economical.

Figure 4C:
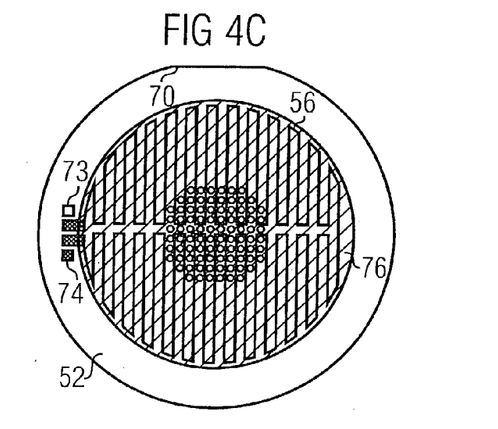

As shown in FIG. 4C, a chemically resistant waterproof insulating layer 76 is next applied over the heater. This layer must be resistant to acid or alkali and must prevent the liquid under test from reaching the heater 56. A cermet insulator may be applied by screen printing. Preferably, the insulator 76 is double-printed to reduce the chance of pinholes allowing the liquid under test to reach the heater 56. The insulator preferably overlaps slightly on all sides of the heater.

Figure 4D:
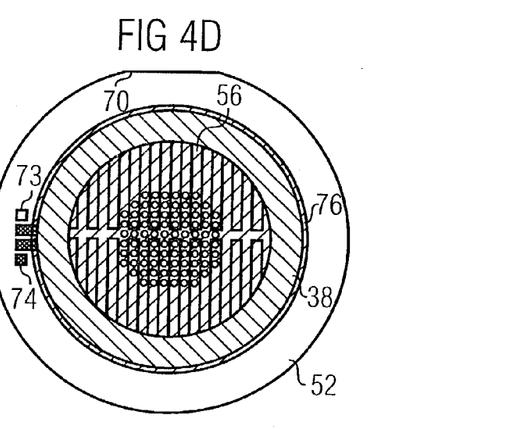

FIG. 4D shows the electrode 38, in this case made of platinum by screen-printing platinum-rich paste and heating. The platinum electrode is formed in electrical contact with one of the through-plated holes 74. The platinum electrode is preferably annular, concentric with the substrate. The electrode may have an outside diameter of about 52 mm and an inside diameter of about 43 mm. Other materials and methods could, of course, be used to provide the electrode 38.

Figure 4E:
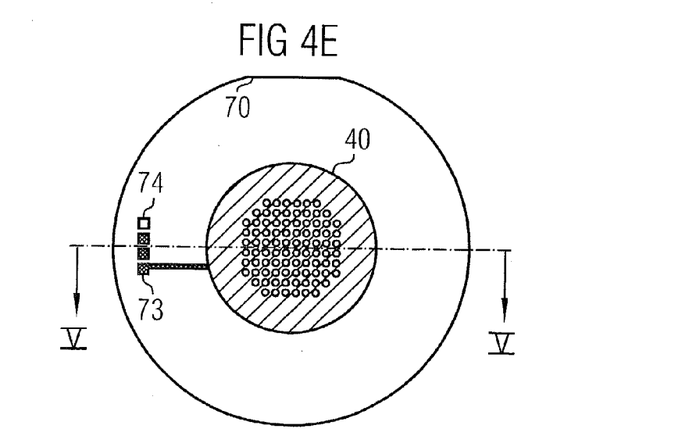

FIG. 4E shows a view of the upper surface of the integrated element, showing the formation of the electrode 40. This electrode may be fabricated with identical materials and methods to those used to produce the electrode 38. For example, platinum-rich paste may be screen printed onto the substrate and baked. The electrode must be in electrical connection with a contact 73. Preferably, the electrode 40 is provided around and between the holes 72, but with a certain clearance to ensure that the paste does not foul the holes. A clearance of 0.25 mm may be sufficient. In this example, the electrode 40 may have an outer diameter of 30 mm.

Figure 5:
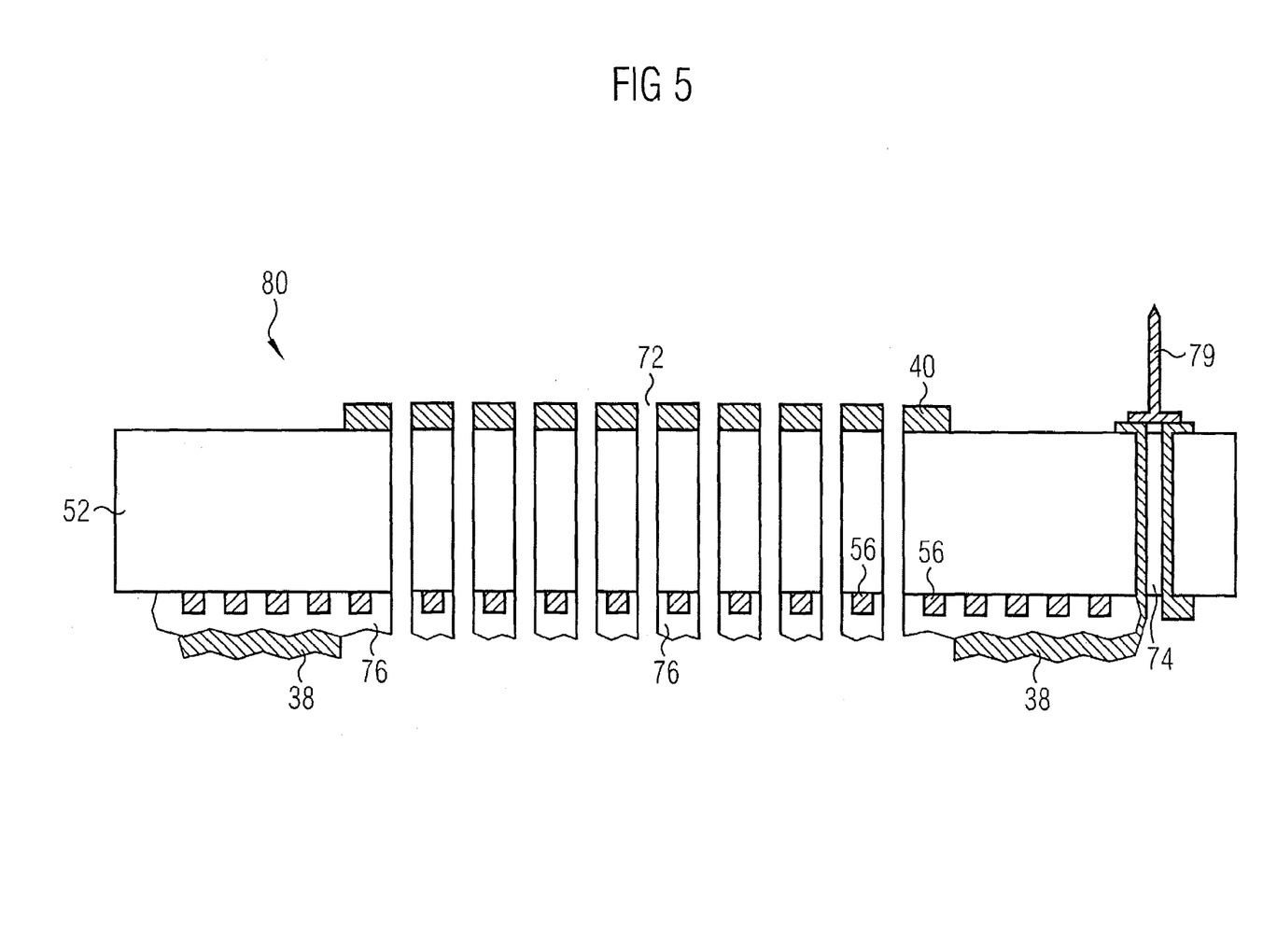
FIG. 5 shows a cross section through an integrated element of FIG. 4.

FIG. 5 shows a cross-section through the integrated element 80 of FIG. 4E, along the line V—V. Features corresponding to those illustrated in earlier drawings carry corresponding reference numerals. Contact pins 79 may be provided, in respective contact with the pads and through-holes 73, 74, to facilitate electrical connection to the electrodes 38, 40 and the heater 56. The integrated element may accordingly be seen to embody numerous features of the structure of the invention illustrated in FIG. 3.

Figure 6:
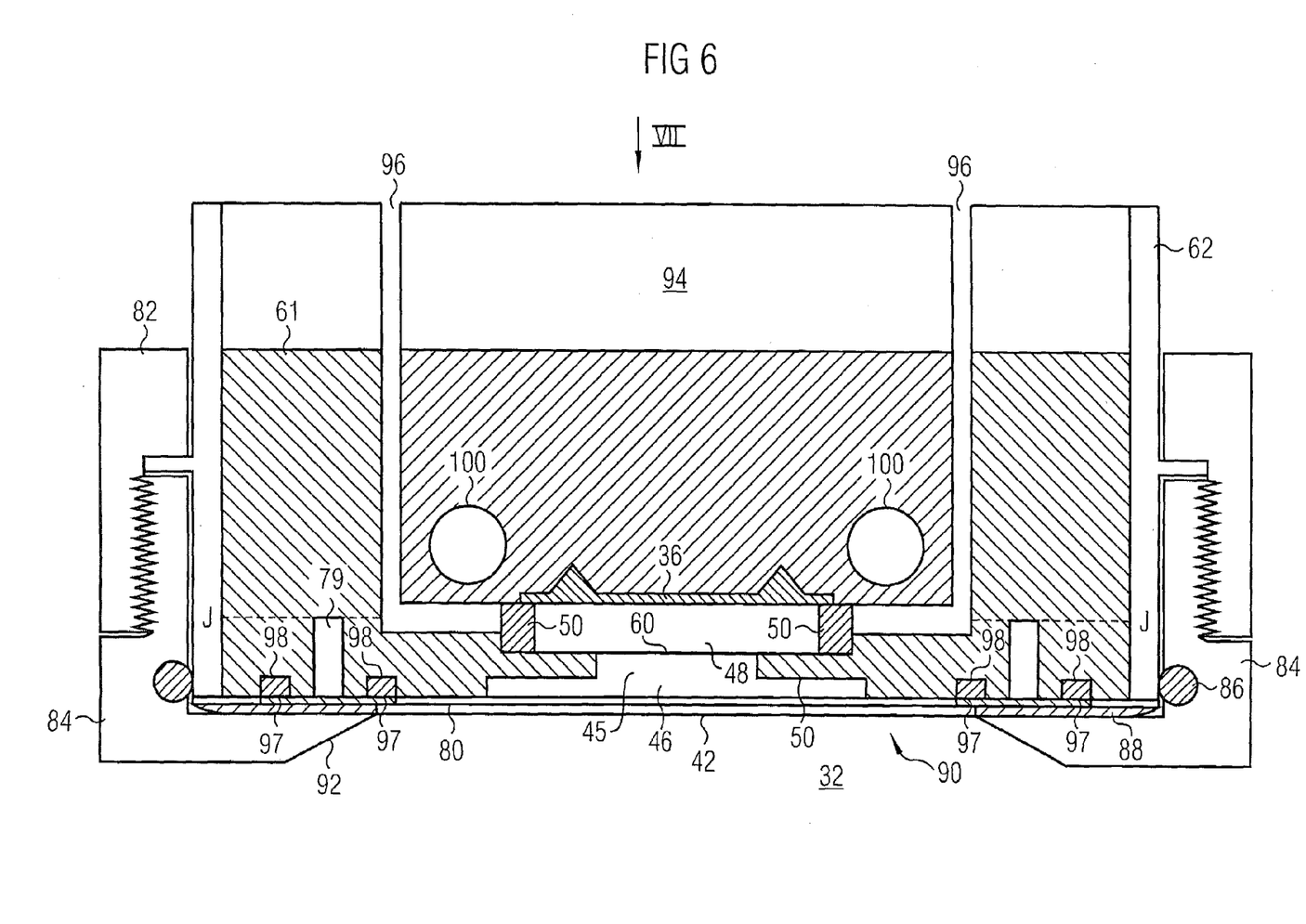
FIG. 6 shows a sample preparation and measurement device according to an embodiment of the present invention.

FIG. 6 shows an example of a practical detection device incorporating the present invention. Outer casing 62, preferably of stainless steel, nylon or another material which is mechanically strong but resistant to corrosion, carries a threaded ring 82 against which a threaded end piece 84 may be tightened. Semi-permeable membrane 42, which is preferably hydrophilic, is placed across the open end of casing 62 and may be pulled tight by action of o-ring 86 when end-piece 84 is tightened. Preferably, threaded ring 82 is rotated while end-piece 84 is held stationary. This allows the membrane 42 to be tightened without imparting any rotational forces to it. An integrated element 80, such as that shown in FIGS. 4–5, is provided, isolated from the liquid under test 32 by the semipermeable membrane 42. The membrane 42 is spaced away from the assembly 80 by the thickness of a gasket 88 which is brought into compression by the action of end-piece 84 when tightened. End-piece 84 has an open window 90 allowing access by the liquid 32 to the membrane 42. Preferably, the edges 92 of the window are chamfered to reduce the likelihood of a build-up of bio-fouling or solid matter, and to promote free circulation of the liquid 32 in the vicinity of the membrane 42. Liquid is able to traverse the integrated element 80 and enter the sample volume 45. Gas permeable membrane 60 allows access by the ammonia, or other gas produced as appropriate, into the gas volume 48, which is at least partly exposed to sensor 36. The gas permeable membrane 60 preferably comprises a hydrophobic, protein resistant membrane, for example it may comprise a porous Teflon™ hydrophobic membrane. The membrane is preferably protein resistant to reduce or prevent the build-up of bio-fouling on the membrane. A porous ring 50 is preferably provided, to retain the measurand gas within the space 48, while allowing it to out-diffuse with time through vents 96. Sensor 36 detects the measurand species, such as ammonia, and produces a corresponding output according to the type of sensor used. Electrical contacts 79 affixed to the integrated element 80 provide electrical connection to the electrodes 38, 40 and any heater 56 present on the integrated element 80. The device is also preferably heated by a heater 100 to prevent condensation of water vapour and other gases in the body of the sample preparation device. A block 61 retains the heater and the various components in place. It contains a cavity defining the sample volumes 48, 45. The block should be of a corrosion resistant material. In order to assist in maintaining a constant temperature, the block may be of a material with a high thermal coefficient. For example, the block may be of brass, stainless steel or a plastic such as polyethyl-etherketone ("peek"). The block may be formed in two or more parts, for example, joined along line J—J, to facilitate manufacture and assembly operations. A body 94 closes the housing 62, but allows egress of gas through vents 96. The body 94 houses various electronic components required for the control and measurement functions; and also contains a power supply to provide power to the sensor 36, the electrodes and the electronics in body 94. O-rings 97 located in grooves 98 in the block 61 may be provided, sealing between the integrated element 80 and the block 61, preventing ingress of the measurand fluid 32 other than by way of the membrane 42.

In a certain embodiment, the integrated element 80 may have a diameter of 66.2 mm, and the entire structure shown in FIG. 6 may have a diameter of 110 mm. In this case, the housing 62 may have an inside diameter of 82 mm and an outside diameter of 88 mm.

Figure 7:
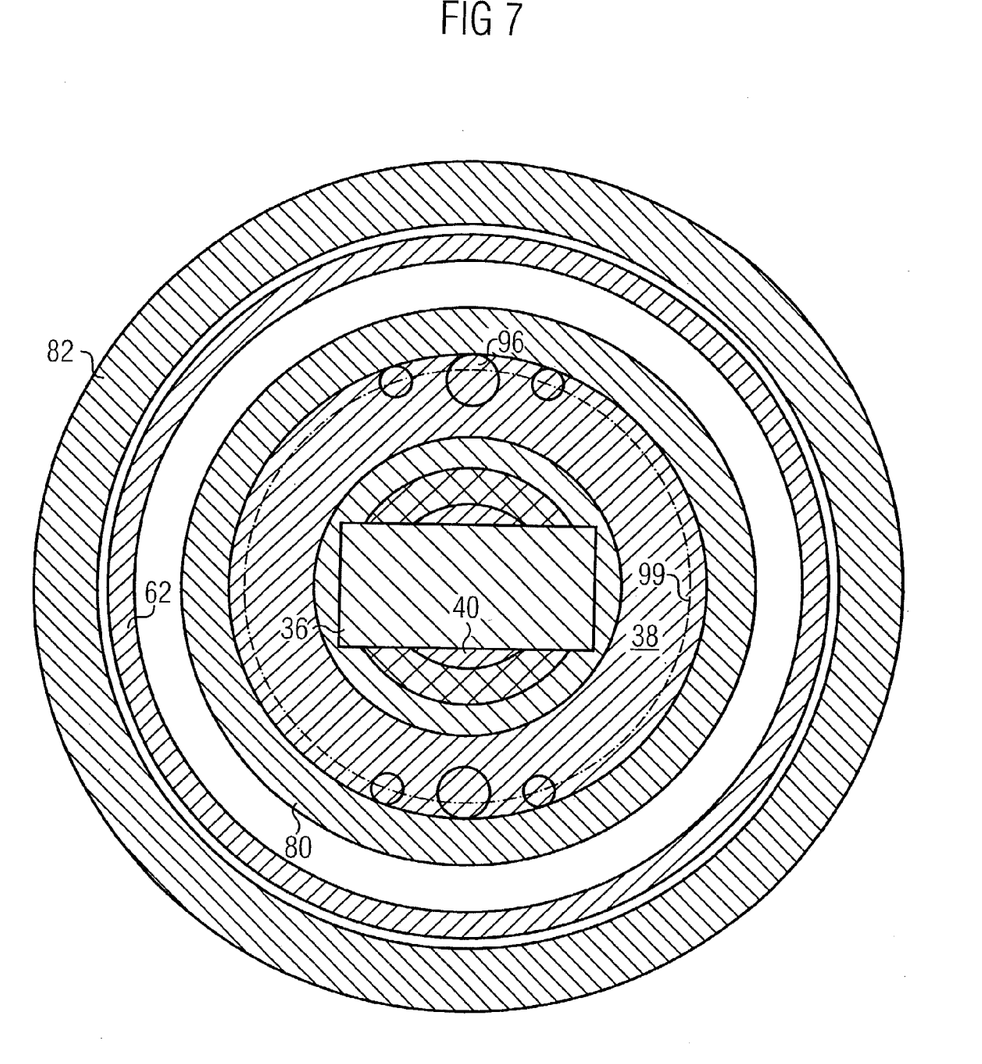
FIG. 7 shows another view of the device of FIG. 6.

FIG. 7 shows a view of the device of FIG. 6 in the direction of arrow VII. Dotted line 99 shows the region of the integrated element 80 which is exposed to the sample volume 45. The other features bear reference numerals corresponding to the reference numerals employed in the preceding drawings.

The present invention accordingly provides a sample preparation device and method for detection of a broad range of chemicals, particularly those which become volatile under certain conditions of pH and temperature. Some examples include ammonium ions ($NH_4^+$) and ammonia ($NH_3$), Chlorine (Cl), Cyanide ($CN^-$) and mono-, di-, and tri-chloramides ($NH_2Cl$, $NHCl_2$, $NCl_3$).

In one embodiment, the gas sensor may be adapted to measure carbon dioxide gas. This provides a means to measure the total inorganic carbon level of an aqueous sample. The acidification of the sample liberates carbon dioxide from any bicarbonates and carbonates present in the sample.

In another embodiment, the gas sensor may instead be adapted to measure sulphur dioxide gas. Acidification of the sample (to a pH below 0.7) enables the "free" sulphur dioxide levels to be monitored; this is especially useful in the food and drink industries. Samples containing "bound" sulphur dioxide could be analysed by increasing the pH to a value above 12, when sulphur dioxide will be liberated and can be measured. These two techniques could be combined to provide a measure of the total sulphur dioxide levels; both measurements could be made simultaneously with the present invention.

The invention finds application in monitoring water treatment processes, or measuring concentrations of certain chemicals in industrial effluent, or monitoring chemicals in water supplies.

The present invention accordingly provides, in certain preferred embodiments, an assembly including a hydrophilic membrane to protect the electrodes from suspended solids in the sample, a thin electrode assembly to achieve a faster response and the addition of a heater for temperature control to achieve consistent detection conditions and improved anti-fouling properties.

By way of examples only, the following materials could be used for the hydrophobic and hydrophilic membranes, although these examples are not limiting of the invention in any way, and other materials may be used for the membranes, as appropriate. The hydrophobic membrane may be formed from commonly available hydrophobic PTFE (polytetrafluoroethylene) membrane. Similarly, the hydrophilic membrane may be formed from hydrophilic PTFE. In a specific example, the following material may be used. Certain characteristic properties of the material are also listed.

| | |
|---|---|
| Filter Medium: | Hydrophilic polysulfone |
| Pore Size: | 0.2 μm to 0.45 μm |
| Typical Thickness: | 165 μm |
| Typical Water Flow Rate: | for pore size 0.2 μm: 12 mL/min/cm$^2$ at 0.7 bar |
| | for pore size 0.45 μm: 50 mL/min/cm$^2$ at 0.7 bar |
| Maximum Operating Temperature-Water: | 121° C. |
| Extractables-Boiling Water: | <3.5% |
| Minimum Bubble Point-Water: | for pore size 0.2 μm: 2.5 bar |
| | for pore size 0.45 μm: 1.5 bar |
| Biological Safety: | Passes USP Class VI-121° C. Plastics Tests |

While the present invention has been particularly described with reference to the detection of dissolved species in water, it may be applied to the detection of species dissolved in other fluids, in which case references to "water", "waterproof" "hydro-" etc. should be construed as appropriate.

The invention claimed is:

1. A device for detection of impurities in an impure liquid, comprising: a first electrode (40) and a second electrode (38) located for immersion in a liquid under test (32); a semipermeable membrane (42) positioned to delimit a sample volume (46) from a body of the liquid under test, said semipermeable membrane allowing the liquid under test to pass therethrough to reach the sample volume, while preventing solids carried in the liquid from reaching the sample volume; and a sensor comprising a sensing element accessible to the sample volume, characterised in that an integrated element, comprising a porous or permeable substrate carrying the first electrode and a heater, is provided within the sample volume.

2. A device according to claim 1 wherein the semipermeable membrane also prevents the solids from reaching the second electrode (38).

3. A device according to claim 2 wherein the integrated element further carries the second electrode.

4. A device according to claim 3 wherein the integrated element itself comprises: the porous or permeable substrate (52) ; the first electrode (40) formed on a first side of the substrate; and the second electrode formed on a second side of the substrate.

5. A device according to claim 4 wherein the integrated element further comprises the heater element (56) located between one of the sides of the substrate and the corresponding electrode, the heater element being insulated (76) from the corresponding electrode.

6. A device according to claim 4, wherein the electrodes and the heater element are formed by deposition of respective conductive layers onto the substrate.

7. A device according to claim 1, wherein the first and second electrodes are planar and concentric, the first electrode being substantially circular, the second electrode being substantially annular, having an inside diameter larger than the diameter of the first electrode.

8. A device according to claim 1, wherein a gas volume (48) is provided between the first electrode (40) and the sensor (36).

9. A device according to claim 8 wherein a gas permeable membrane (60) is provided to prevent the liquid in the sample volume from entering the gas volume, while allowing any gas emanating from the liquid to enter the gas volume.

10. A device according to claim 9, wherein the gas permeable membrane (60) is hydrophobic.

11. A device according to claim 1, wherein the substrate comprises physical barrier (52) between the first and second electrodes..

12. A device according to claim 11 wherein the physical barrier is porous or permeable to the liquid under test.

13. A device according to claim 1, further comprising a barrier (50) around the first electrode, for restricting the movement of the liquid under test.

14. A device according to claim 1, further comprising a second heater (100) for preventing condensation of vapour generated from the liquid under test.

15. A device according to claim 1, further comprising an ion sensitive electrode as the sensor.

16. A device according to claim 1, further comprising a selective gas detector as the sensor.

17. A device according to claim 1, wherein the semipermeable membrane (42) is hydrophilic, at least on the side which is directed away from the sample volume.

18. A device according to claim 1, comprising means for measuring and controlling at least one of the following characteristics of the liquid under test in the region of the first electrode: pH, temperature, conductivity.

19. A device according to claim 1, further comprising an outer housing (62) to contain the electrodes, substrate, heater, membrane and sensor.

* * * * *